(12) United States Patent
Long

(10) Patent No.: US 11,512,044 B2
(45) Date of Patent: Nov. 29, 2022

(54) METHOD FOR PREPARING SALICYLAMINE ACETATE

(71) Applicant: TSI Group, Co., Ltd., Jiangsu (CN)

(72) Inventor: Ling Long, Shanghai (CN)

(73) Assignee: TSI GROUP CO., LTD., Jiagyin (CN)

( * ) Notice: Subject to any disclaimer, the term of this patent is extended or adjusted under 35 U.S.C. 154(b) by 0 days.

(21) Appl. No.: 16/768,570

(22) PCT Filed: Nov. 26, 2018

(86) PCT No.: PCT/CN2018/117458
§ 371 (c)(1),
(2) Date: Oct. 28, 2020

(87) PCT Pub. No.: WO2019/105324
PCT Pub. Date: Jun. 6, 2019

(65) Prior Publication Data
US 2021/0053907 A1 Feb. 25, 2021

(30) Foreign Application Priority Data

Nov. 28, 2017 (CN) .......................... 201711221319.7

(51) Int. Cl.
*C07C 231/10* (2006.01)
*C07C 235/34* (2006.01)

(52) U.S. Cl.
CPC .......... *C07C 231/10* (2013.01); *C07C 235/34* (2013.01)

(58) Field of Classification Search
None
See application file for complete search history.

(56) References Cited

U.S. PATENT DOCUMENTS 6,117,880 A * 9/2000 Guo ..................... C07D 221/20
514/278

FOREIGN PATENT DOCUMENTS

JP 55162747 A 12/1980
WO 2012104305 A1 8/2012

OTHER PUBLICATIONS

Greene's Protective Groups in Organic Synthesis (John Wiley & Sons, Inc., 4th Ed., 2007, p. 725-731 and 748-756) (Year: 2007).*
Supporting Information for Mestichelli et al., Org. Lett., 2013, 15(21), 5448 (Year: 2013).*
Mestichelli et al., Org. Lett., 2013, 15(21), 5448 (Year: 2013).*
Zagol et al. (Chem. Res. Toxicol., 2010, 23, 240) (Year: 2010).*
Lee et al., "Colorimetric anion sensing by porphyrin-based anion receptors", Tetrahedron Letters, 2001, pp. 8665-8668, vol. 42.
Zagol-Ikapitte et al., "Characterization of Scavengers of y-Ketoaldehydes That do Not Inhibit Prostaglandin Biosynthesis", Chem. Res. Toxicol., 2010, vol. 23, No. 1.
Mestichelli et al., "Concise Copper-Catalyzed Synthesis of Tricyclic Biaryl Ether-Linked Aza-Heterocyclic Ring Systems", Organic Letter, Oct. 17, 2013, pp. 5448-5451, vol. 15, No. 21, Publisher: American Chemical Society.
Plattner et al., "[(Aminomethyl)aryloxy]acetic Acid Esters. A New Class of High-Ceiling Diuretics", Journal of Medicinal Chemistry, Dec. 31, 1984, vol. 27, No. 12.

* cited by examiner

*Primary Examiner* — Sudhakar Katakam
*Assistant Examiner* — Jennifer C Sawyer
(74) *Attorney, Agent, or Firm* — Emily E. Harris; Matthew W. Coryell

(57) ABSTRACT

Disclosed is a method for preparing salicylamine acetate. The method comprises the steps of: (1) carrying out amino protection on salicylaldehyde having a structure represented by formula 1 to obtain a compound having a structure represented by formula 2; and (2) carrying out acid hydrolysis to the compound having a structure represented by formula 2 and then reacting the acid-hydrolyzed compound with acetic acid to obtain salicylamine acetate.

10 Claims, 3 Drawing Sheets

METHOD FOR PREPARING SALICYLAMINE ACETATE

TECHNICAL FIELD

The present disclosure pertains to the field of chemical synthesis, more particularly to a method for preparing salicylamine acetate.

BACKGROUND ART

Salicylamine acetate has a structural formula represented by

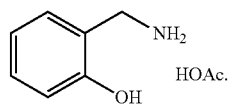

If it's prepared by way of reduction using salicylaldoxime as a starting material, hydrogen reduction, zinc powder reduction or palladium on carbon reduction will be involved. However, when a Raney nickel catalyst is used, the main product of hydrogen reduction in the presence of aqueous ammonia is a compound having a structure shown by Formula 4. Also with the use of a Raney nickel catalyst, no product is obtained from hydrogen reduction in the presence of $Boc_2O$, and only the starting material, salicylaldoxime, remains. When zinc powder reduction is employed, salicylaldoxime reacts with ammonium formate in methanol to form a compound having a structure shown by Formula 4 as the main product. In zinc powder reduction, the reaction with glacial acetic acid, no matter at 15° C., or 40° C., or 80° C., provides no product, and only the starting material, salicylaldoxime, remains. In palladium on carbon reduction, the reaction of salicylaldoxime with a solution of hydrochloric acid under hydrogen only provides a small amount of the target product, and a large amount of the starting material, salicylaldoxime, remains. If salicylonitrile is used as a starting material, the target product is obtained by reduction with lithium aluminum hydride in tetrahydrofuran and subsequent reaction with glacial acetic acid in ethanol. However, lithium aluminum hydride is dangerous to operate, and a large quantity of solid waste and hydrogen will be generated when lithium aluminum hydride is quenched, leading to increased challenges of safety and environmental protection. Moreover, such a process incurs high cost, and thus is difficult to be industrialized.

Therefore, there is an urgent need in the art to provide a method for preparing salicylamine acetate, wherein the method needs to be cost effective, environmentally friendly and suitable for industrial production.

SUMMARY

The present disclosure aims to provide a novel method for preparing salicylamine acetate.

The disclosure provides a method for preparing salicylamine acetate, comprising the following steps:

(1) subjecting salicylaldehyde of Structural Formula 1 to amino protection to obtain a compound of Structural Formula 2; and (2) subjecting the compound of Structural Formula 2 to acid hydrolysis, followed by reaction with acetic acid to obtain salicylamine acetate:

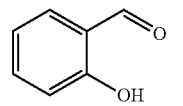

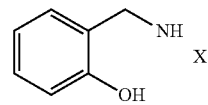

wherein X = Cbz or Boc.

In another preferred embodiment, the amino protection in Step (1) is performed at a reaction temperature of 0-50° C.

In another preferred embodiment, the amino protection in Step (1) is performed for a reaction time of 3-18 hours.

In another preferred embodiment, an equivalent ratio of tert-butyl carbamate to salicylaldehyde in Step (1) is 1.0-3.0:1.

In another preferred embodiment, a reaction solvent selected from the group consisting of tetrahydrofuran, 2-methyltetrahydrofuran, acetonitrile and 1,4-dioxane is used in Step (1).

In another preferred embodiment, an acid selected from the group consisting of hydrochloric acid, trifluoroacetic acid, hydrobromic acid and sulfuric acid is used for the hydrolysis in Step (2).

In another preferred embodiment, the acid hydrolysis in Step (2) is performed in the presence of an alcoholic organic solvent, wherein the alcoholic organic solvent is a C1-4 aliphatic alcohol; more preferably, the alcoholic organic solvent is selected from methanol, ethanol and n-butanol.

In another preferred embodiment, the reaction with acetic acid in Step (2) is performed at a temperature ranging from room temperature to the reflux temperature of the acetic acid solution.

In another preferred embodiment, the reaction with acetic acid in Step (2) is performed for a reaction time of 10-24 hours.

Therefore, the present disclosure provides a method for preparing salicylamine acetate, wherein the method is cost effective, environmentally friendly and suitable for industrial production.

DETAILED DESCRIPTION

Figure 1:
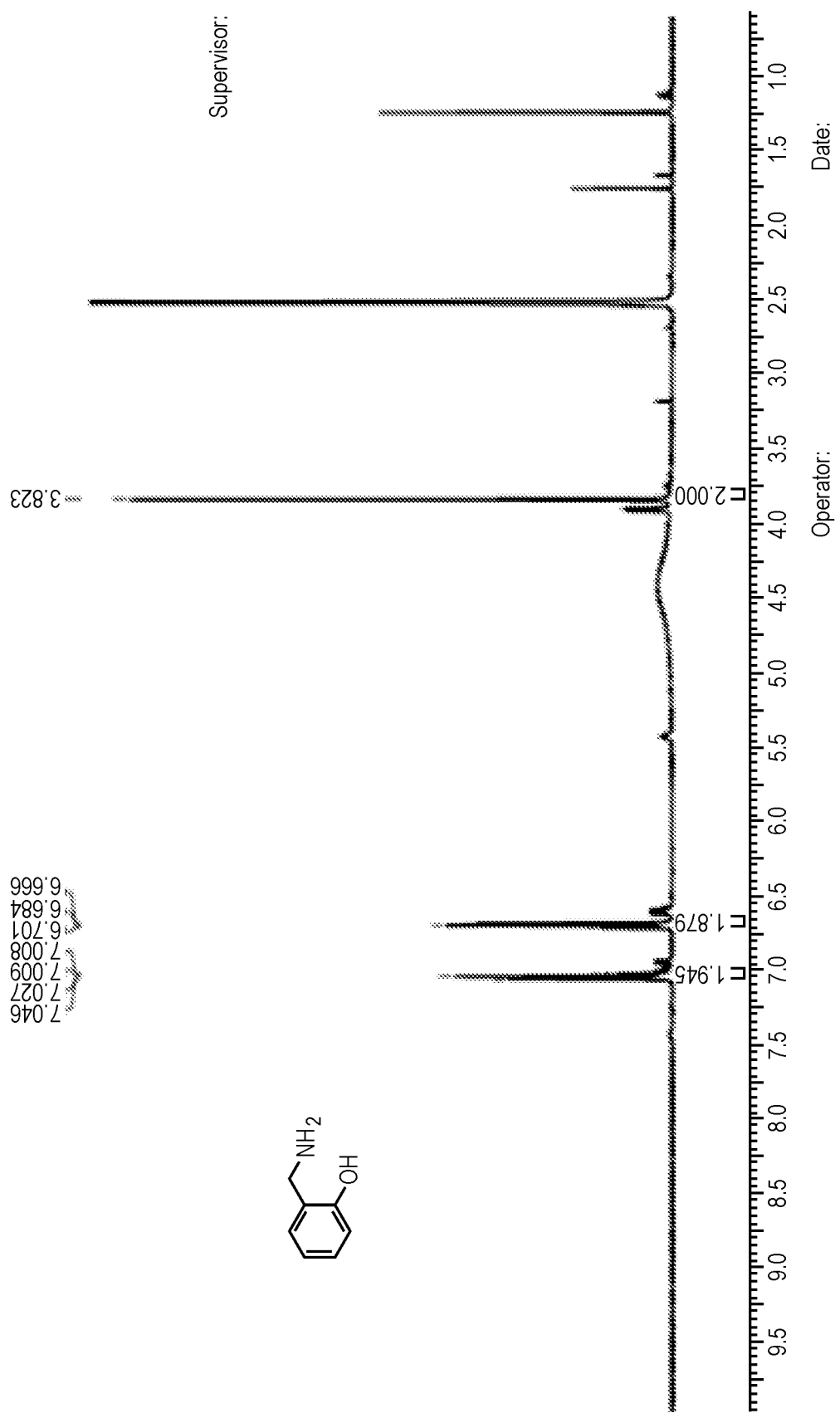
FIG. 1 shows an NMR spectrum of salicylamine obtained according to the method provided by the present disclosure.

After extensive and intensive research, the inventor has discovered that salicylamine acetate can be conveniently and efficiently obtained from salicylaldehyde as a starting material, with the use of an amino-protecting agent and the process of acid hydrolysis. This method can be put into industrial production. The invention is accomplished on such a basis.

The compounds involved in the present disclosure are listed in the following table:

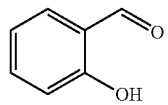
1

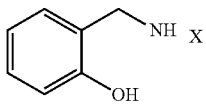
2 wherein X = Cbz or Boc

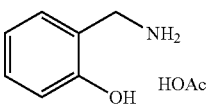
3

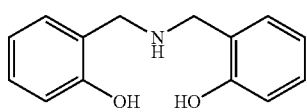 [SMILES: Oc1ccccc1CNCc1ccccc1O]
4

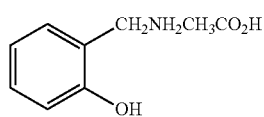
5

In particular, the method for preparing salicylamine acetate of Structural Formula 3 provided by the present disclosure includes the following steps:

Step 1, mixing salicylaldehyde of Structural Formula 1 with an amino-protecting agent to obtain the compound of Structural Formula 2; and Step 2, mixing the compound of Structural Formula 2 with an acid or an acid solution to obtain a product which is then contacted with acetic acid to obtain salicylamine acetate of Structural Formula 3.

In an embodiment of the present disclosure, the mixed system of salicylaldehyde of Structural Formula 1 and the amino-protecting agent formed in Step 1 comprises a solvent selected from the group consisting of tetrahydrofuran, 2-methyltetrahydrofuran, acetonitrile and 1,4-dioxane.

In an embodiment of the present disclosure, the mixed system of salicylaldehyde of Structural Formula 1 and the amino-protecting agent formed in Step 1 further comprises triethylsilane.

In an embodiment of the present disclosure, the mixed system of salicylaldehyde of Structural Formula 1 and the amino-protecting agent formed in Step 1 further comprises trifluoroacetic acid.

In an embodiment of the present disclosure, the mixing temperature in Step 1 is 0-50° C., preferably 10-50° C.

In an embodiment of the present disclosure, the mixing time in Step 1 is 3-18 hours, preferably 8-18 hours.

In an embodiment of the present disclosure, Step 1 comprises mixing salicylaldehyde of Structural Formula 1, an amino-protecting agent, triethylsilane and trifluoroacetic acid, and holding the resulting system at a temperature of 0-50° C. (preferably 10-50° C.) for 3-18 hours (preferably 8-18 hours) to obtain the compound of Structural Formula 2, wherein the amino-protecting agent is selected from benzyl carbamate or t-butyl carbamate; wherein the equivalent ratio of the amino-protecting agent to salicylaldehyde used is 1.0-3.0:1; and wherein the equivalent ratio of triethylsilane to salicylaldehyde used is 1.0-3.0:1.

In a preferred embodiment of the present disclosure, the system is stirred while the temperature is being held.

When tert-butyl carbamate is used in Step 1, mixing is performed in an organic solvent selected from the group consisting of tetrahydrofuran, 2-methyltetrahydrofuran, acetonitrile, and 1,4-dioxane.

In a preferred embodiment of the present disclosure, the reaction for obtaining the compound of Formula 2 is quenched with a saturated inorganic base solution in Step 1, wherein the inorganic base is selected from the group consisting of sodium bicarbonate, potassium bicarbonate, potassium carbonate, sodium carbonate, sodium hydroxide, lithium hydroxide, etc.; wherein the inorganic base solution is used in any amount so long as the reaction can be quenched, preferably in such an amount that the system is weakly alkaline, for example, the system has a pH of 7-9, 7-8.5, 7-8, 7.5-8.5, 7.5-9, etc.

In an embodiment of the present disclosure, the acid solution in Step 2 is an aqueous solution of an acid, wherein the acid is selected from the group consisting of hydrochloric acid, trifluoroacetic acid, hydrobromic acid and sulfuric acid.

In an embodiment of the present disclosure, the compound of Structural Formula 2 is mixed with an acid or an acid solution in a C1-4 aliphatic alcohol at a mixing temperature of 5-40° C. (preferably 10-35° C.).

In an embodiment of the present disclosure, Step 2 comprises mixing the compound of Structural Formula 2 with an acid or an acid solution in a C1-4 aliphatic alcohol (preferably methanol, ethanol or n-butanol); quenching the reaction with an inorganic base; extracting the reaction solution with an organic solvent to obtain an organic phase; and mixing the organic phase with acetic acid to allow for reaction at a temperature ranging from room temperature to reflux temperature for 10-16 hours, thereby providing salicylamine acetate of Structural Formula 3. The inorganic bases include sodium bicarbonate, potassium bicarbonate, potassium carbonate, sodium carbonate, sodium hydroxide, lithium hydroxide, etc. The inorganic base may be used in any amount so long as the reaction can be quenched, preferably in such an amount that the system is weakly alkaline, for example, the system has a pH of 7-9, 7-8.5, 7-8, 7.5-8.5, 7.5-9, etc. The organic solvents used for the extraction include 2-methyltetrahydrofuran, ethyl acetate, dichloromethane and the like.

In a preferred embodiment of the present disclosure, to the system where acetic acid has been mixed, methyl tert-butyl ether is added to allow for crystallization. After filtration, salicylamine acetate having relatively higher purity is obtained.

The above features mentioned in the disclosure or the features mentioned in the Examples may be combined arbitrarily. All of the features disclosed in the specification of this application may be used in combination with any composition, and the various features disclosed in the specification may be replaced with any alternative features that can serve the same, equivalent or similar purposes. Therefore, unless otherwise stated, the disclosed features are only general examples of equivalent or similar features.

The main advantages of the present disclosure include:

1. The method provided by the present disclosure for preparing salicylamine acetate can be industrialized.

2. The salicylamine acetate obtained by the method of the present disclosure has good appearance.

The invention will be further illustrated with reference to the following specific Examples. It's to be understood that these Examples are only intended to demonstrate the present disclosure without limiting the scope of the present disclosure. The experimental methods in the following examples for which no specific conditions are indicated will be carried out generally under conventional conditions or under those conditions suggested by the manufacturers. Unless otherwise indicated, all percentages, ratios, proportions, or parts are based on weight. The unit of weight volume percentage in the present disclosure is well known to those skilled in the art. For example, it refers to the weight of a solute in 100 ml of a solution. Unless otherwise defined, all professional and scientific terms used herein have the same meanings as known to those skilled in the art. In addition, any methods and materials similar to or equivalent to those described herein can be applied to the method of the present disclosure. The preferred methods and materials described herein for practice of the present disclosure are intended only for the purpose of demonstration.

Example 1

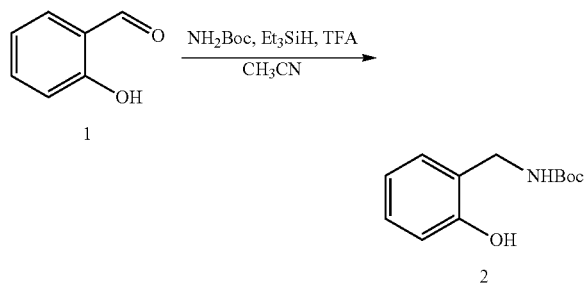

Acetonitrile (168.0 g) and the main raw material, salicylaldehyde (70.4 g, 1.00 eq), were added to a 1 L reaction flask. Tert-butyl carbamate (74.0 g, 1.10 eq) and triethylsilane (79.0 g, 1.20 eq) were added to the 1 L reaction flask. Trifluoroacetic acid (65.4 g, 1.00 eq) was added dropwise to the reaction system under a controlled temperature of 15° C. to 40° C. After the dropwise addition, the system was held at 15-40° C. with agitation for 12-16 hours before sampling began. Sampling was performed every 2-4 hours. HPLC was used to trace the amount of the starting material until the content of the starting material was <5% or the variation between two consecutive samples was <1%. To the system was added 525 g of a saturated sodium bicarbonate solution (490 g water+35 g sodium bicarbonate) under a controlled temperature of 15 to 30° C. to quench the reaction (the specific addition amount depended on pH, wherein pH=7-8). Then, the reaction solution was extracted twice with ethyl acetate which was added in an amount of 252 g each time. The organic phases were combined, and washed with 280 g water and 336 g saturated brine (252 g water+84 g sodium chloride) respectively. 100 g anhydrous sodium sulfate was added to the brine-washed organic phase, followed by stirring and drying for 2-4 hours. Then, centrifugation or suction filtration was performed. The filter cake was rinsed with 63 g ethyl acetate. The filter cake was put aside temporarily, and the filtrates were combined for use in the next step (in Example 2).

Example 2

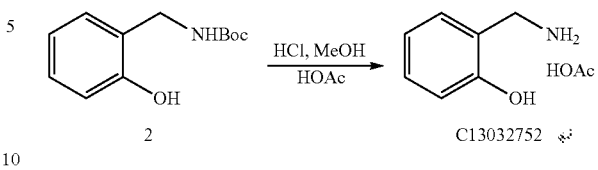

At 15-30° C., methanol (350 ml) and the crude product (1.00 eq) obtained in Example 1 were added to a 1 L reaction flask. Water (50 ml) and concentrated hydrochloric acid (100 ml, 2.00 eq) were added to the 1 L reaction flask. After stirring at 15-30° C. for 16 hours, sampling was conducted until the content of the starting material was <0.5% as detected by HPLC. After the reaction was over, the system was concentrated to remove methanol. 500 ml water was added to the concentrated system which was dissolved to form a homogeneous phase. Then, the resulting mixture was extracted with ethyl acetate (350 ml*2). After the extraction, the aqueous phase was to be adjusted to be alkaline. Particularly, 85 g sodium bicarbonate was added to adjust the pH to 7-8. Extraction was performed 4 times with 2-methyltetrahydrofuran which was added in an amount of 700 ml each time. The organic phase was concentrated to dry to obtain a yellow solid. The yellow solid was dissolved in 350 ml acetic acid, and stirred for 16 hours at 15-30° C. 1000 ml methyl tert-butyl ether was added to the system, and precipitation of a solid was observed. After stirring at 15-30° C. for 1-2 hours, suction filtration was performed. The filter cake was rinsed with methyl tert-butyl ether and dried to produce a 42 g product.

$^1$H NMR: DPC0126-31-P1A 400 MHz DMSO-d$_6$
$^1$H NMR (400 MHz, DMSO-d$_6$) δ=7.14-7.04 (m, 2H), 6.78-6.68 (m, 2H), 3.85 (s, 2H), 1.82 (s, 3H)

Example 3

1. Acetonitrile (168.0 g) and the main starting material, salicylaldehyde (70.4 g), were added to a 1500 ml flask.
2. Tert-butyl carbamate (74.0 g) and triethylsilane (79.0 g) were added to the 1500 mL flask.
3. While the temperature was controlled at 10° C.-40° C., trifluoroacetic acid (65.4 g) was added dropwise to the reaction system.
4. After the dropwise addition, the system was held at 10-40° C. with agitation for 10-20 hours before sampling began. Sampling was performed every 2-4 hours. HPLC was used to trace the amount of the starting material until the content of the starting material was <5%.
5. The temperature was controlled at 15-40° C. To the system was added 525 g of a saturated sodium bicarbonate solution to quench the reaction. Then, the reaction solution was extracted twice with ethyl acetate which was added in an amount of 252 g each time. The organic phases were combined, and washed with 280 g water and 336 g saturated brine respectively. 100 g anhydrous sodium sulfate was added to the brine-washed organic phase, followed by stirring and drying for 2-4 hours. Then, centrifugation or suction filtration was performed. The filter cake was rinsed with 65 g ethyl acetate.

Example 4

1. While the temperature was controlled at 5-25° C., concentrated sulfuric acid (84.4 g) was added dropwise to the ethyl acetate filtrate obtained in Example 3 after drying.

2. After the dropwise addition, the system was held at 5-25° C. with agitation for 10-20 hours before sampling began. Sampling was performed every 2-4 hours. HPLC was used to trace the amount of the starting material until the content of the starting material was <2%.

3. The post-reaction system was centrifuged. The centrifuged solid was added to an enamel vessel, washed with 252 g ethyl acetate under agitation, and centrifuged again. The centrifuged solid was dried to obtain a 98 g sulfate.

4. After drying, the sulfate was dissolved in 1155 g anhydrous methanol under agitation to obtain a clear solution, and then 112 g solid sodium bicarbonate was added.

5. The system was stirred at 10-30° C. for 16-24 hours. After sampling for nuclear magnetic detection, the result showed that the system was completely free, and salicylamine was obtained. See FIG. 1.

6. 20 g diatomite was added to the completely free system. After cooling to a temperature of −5 to 5° C., the system was stirred for 3-5 hours, and then centrifuged directly. The centrifuged solid was rinsed with 78 g methanol.

7. The centrifuged mother liquor was vacuum concentrated until no fraction came out, and 150 g methyl tert-butyl ether was added.

8. The system was stirred at 5-15° C. for 2-4 hours and then centrifuged. The centrifuged solid was rinsed with 75 g methyl tert-butyl ether. The centrifuged solid was dried at 40-50° C. to obtain a 42 g free state product.

9. The dried solid was dissolved in 420 g glacial acetic acid, and stirred for 16-24 hours.

10. 932 g methyl tert-butyl ether was added to the reaction system, and stirring continued for 4-6 hours at 0-10° C. to allow for crystallization.

11. The system was centrifuged. The centrifuged solid was washed with 250 ml 85% ethanol, and then it was centrifuged again.

12. The centrifuged solid was dried at 40-50° C. to obtain a 35.4 g final product which was white in color.

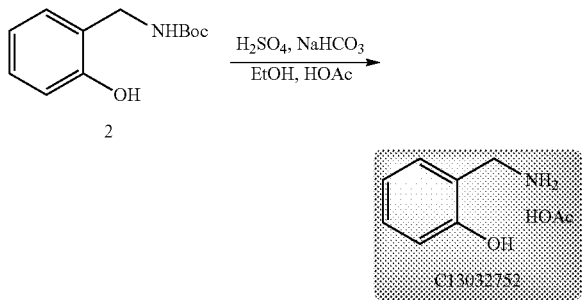

$^1$H NMR: DPC0126-31-P1A 400 MHz DMSO-$d_6$
$^1$H NMR (400 MHz, DMSO-$d_6$) δ=7.14-7.04 (m, 2H), 6.78-6.68 (m, 2H), 3.85 (s, 2H), 1.82 (s, 3H)

Figure 2:
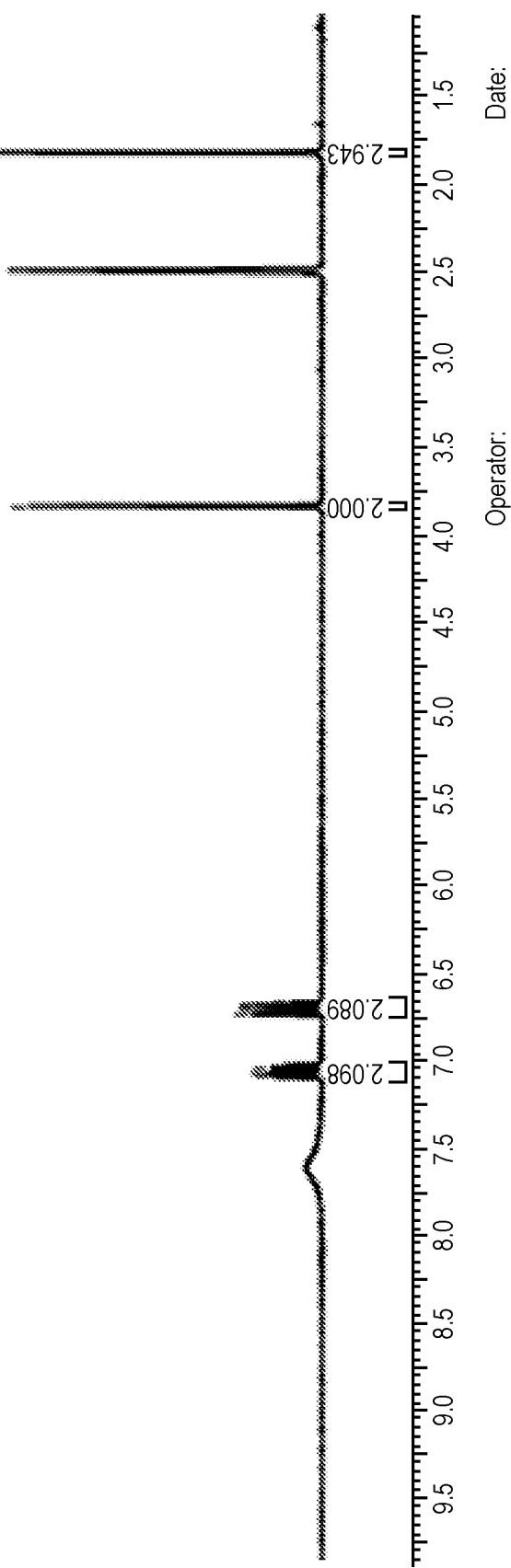
FIG. 2 shows an NMR spectrum of salicylamine acetate obtained according to the present disclosure.
Figure 3:
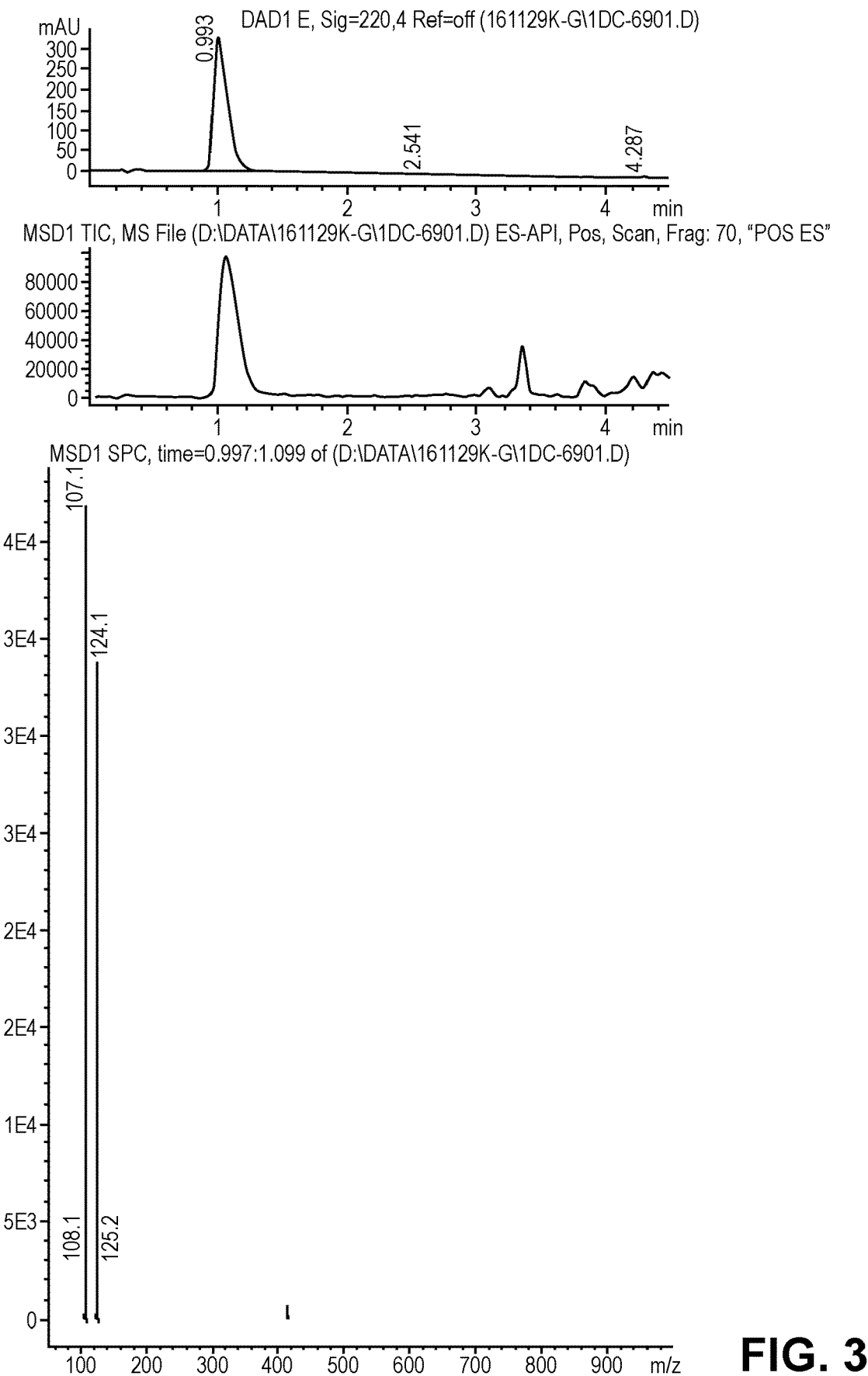
FIG. 3 shows an LC-MS spectrum of salicylamine acetate obtained according to the present disclosure.

Referring to FIGS. 2 and 3, they show that salicylamine acetate with correct structure and height purity was obtained according to the present disclosure.

The examples described above are only preferred ones of the disclosure, and are not intended to limit the scope of the substantive technical contents of the disclosure. The substantive technical contents of the disclosure are generally defined within the scope of the claims in the present application. Any technical entity or method achieved by anyone else will be viewed as falling in the scope of the claims, so long as it is completely the same as one defined within the scope of the claims in the present application or an equivalent variant.

What is claimed is:

1. A method for preparing salicylamine acetate, wherein the method comprises steps of:
   (1) subjecting salicylaldehyde of Structural Formula 1:

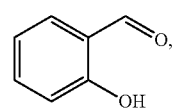

to amino protection to obtain a compound of Structural Formula 2:

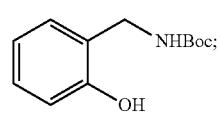

wherein the amino protection is performed with equivalent ratio of tert-butyl carbamate to salicylaldehyde of 1.0-3.0: 1;
   and
   (2) subjecting the compound of Structural Formula 2 to acid hydrolysis, followed by reaction with acetic acid to obtain salicylamine acetate.

2. The method of claim 1, wherein the amino protection in Step (1) is performed at a reaction temperature of 0-50° C.

3. The method of claim 1, wherein the amino protection in Step (1) is performed for a reaction time of 3-18 hours.

4. The method of claim 1, wherein a reaction solvent selected from the group consisting of tetrahydrofuran, 2-methyltetrahydrofuran, acetonitrile and 1,4-dioxane is used in Step (1).

5. The method of claim 1, wherein an acid selected from the group consisting of hydrochloric acid, trifluoroacetic acid, hydrobromic acid and sulfuric acid is used for the hydrolysis in Step (2).

6. The method of claim 1, wherein the acid hydrolysis in Step (2) is performed in the presence of an alcoholic organic solvent.

7. The method of claim 6, wherein the alcoholic organic solvent is a C1-4 aliphatic alcohol.

8. The method of claim 1, wherein the reaction with acetic acid in Step (2) is performed at a temperature ranging from room temperature to the reflux temperature of the acetic acid solution.

9. The method of claim 1, wherein the reaction with acetic acid in Step (2) is performed for a reaction time of 10-24 hours.

10. The method of claim 6, wherein the alcoholic organic solvent is selected from methanol, ethanol, and n-butanol.

* * * * *